(12) United States Patent
Arai et al.

(10) Patent No.: US 10,088,449 B2
(45) Date of Patent: Oct. 2, 2018

(54) ELECTROPHORESIS DEVICE

(71) Applicant: SHIMADZU CORPORATION, Kyoto-shi, Kyoto (JP)

(72) Inventors: Akihiro Arai, Kyoto (JP); Toru Kaji, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 302 days.

(21) Appl. No.: 14/974,647

(22) Filed: Dec. 18, 2015

(65) Prior Publication Data
US 2017/0176382 A1    Jun. 22, 2017

(51) Int. Cl.
*G01N 27/447* (2006.01)

(52) U.S. Cl.
CPC . *G01N 27/44743* (2013.01); *G01N 27/44782* (2013.01)

(58) Field of Classification Search
CPC ............... G01N 27/447; G01N 27/26; G01N 27/44769; G01N 27/44791; G01N 27/44743; B01L 2400/0415; B01L 2400/0421; B01L 3/502761; B01L 2200/0652; B01L 2200/0684; B01L 2200/0668; F15D 1/00; B01D 57/02; C07K 1/26
See application file for complete search history.

(56) References Cited

U.S. PATENT DOCUMENTS

| | | | |
|---|---|---|---|
| 6,635,164 B1 * | 10/2003 | Anazawa | G01N 27/44726 204/600 |
| 7,419,578 B2 * | 9/2008 | Sakai | G01N 27/44782 204/455 |
| 2009/0269767 A1 | 10/2009 | Soderlund et al. | |

FOREIGN PATENT DOCUMENTS

| | | |
|---|---|---|
| JP | H10-148628 A | 6/1998 |
| JP | 2000-131278 A | 5/2000 |
| JP | 3417143 B2 | 6/2003 |
| JP | 2005-315758 A | 11/2005 |
| WO | 2015/134943 A1 | 9/2015 |

\* cited by examiner

*Primary Examiner* — Gurpreet Kaur
(74) *Attorney, Agent, or Firm* — Sughrue Mion, PLLC

(57) ABSTRACT

A capillary electrophoresis device including a capillary tube, a suction pump for taking liquid, an intake tube whose end is formed vertically downward, a connection block in which there is an intake flow path that holds the end of the capillary tube and connecting the suction pump to the intake tube, a sample storage unit which contains a sample and has an upward opening into which the tip of the intake tube may be inserted, an intake tube access mechanism to insert the tip of the intake tube into the sample storage unit, and a voltage application mechanism that applies an electric potential difference across the capillary tube.

12 Claims, 13 Drawing Sheets

ELECTROPHORESIS DEVICE

TECHNICAL FIELD

The present invention relates to an electrophoresis device that conducts electrophoresis analysis using a capillary tube as the cataphoresis channel.

BACKGROUND ART

A capillary electrophoresis device fills a separation medium (which is a buffer solution or a buffer solution containing a screening polymer solution) in a molten silica capillary tube of inner diameter 100 μm or less, and places a sample at one end of the capillary tube, which is separated inside the capillary tube by high voltage applied across the capillary tube. For stabilizing the separation in the capillary tube, the device controls its surrounding temperature precisely. An optical method such as fluorescence analysis or an electrochemical method detects the components of an analyzing object separated in the capillary tube at the other end of the capillary tube.

Introducing a sample into the capillary tube may be carried out by pressure injection from one end or pressure reduction from the other end, and additionally, if a highly viscous separation medium is filled in the capillary tube, an electric filling method which introduces a sample into the capillary tube by applying high voltage across the capillary tube whose one end contacts with a sample solution. (For example, refer to Patent Article 1).

The electric method for filling a sample into a capillary tube introduces a predetermined amount of sample into the capillary tube which is filled with a separation medium by connecting one end of the capillary tube (called the detection end) to a buffer solution reservoir (called the anode reservoir) which contains a buffer solution, and at the same time the other end of the capillary tube (called the injection end) is immersed in a sample storage unit, so that a certain value of electric potential difference may be applied across two electrodes each of which is immersed in the anode reservoir and the sample storage unit respectively for a certain time period.

After introducing the sample into the capillary tube, the injection end is immersed in the reservoir (i.e., the cathode reservoir) which stores a buffer solution, and electrophoresis of the sample is carried out by applying voltage between both electrodes while each of them is immersed in the anode reservoir and the cathode reservoir, respectively.

REFERENCES OF PRIOR ART

Patent Articles

[Parent Article 1] Unexamined Patent Document Publication Number: 2000-131278

SUMMARY OF THE INVENTION

Problems that the Invention is to Solve

As described above, in order to introduce a sample into a capillary tube by applying the electric method, it is necessary to immerse the injection end of the capillary tube and an electrode in the sample storage unit. In particular, when multiple capillary tubes, that is, a plural number of capillary tubes are used, the same number of electrodes are immersed in the sample storage unit at the same time of immersing the capillary tubes, which increases the outer surface area on which the sample adheres to produce contamination caused by taking the sample out of the sample storage unit. For preventing the contamination, the injection ends of the capillary tubes and the electrodes need to be cleaned after introducing a sample into the capillary tubes and after conducting electrophoresis analysis, and therefore, a washing mechanism is required to install.

The capillary tube is coated with a protection film made of polyimide and the like except the visual observation window for optical detection, the coated film may be damaged when the injection end is immersed in the sample storage unit and washed.

Considering these disadvantages of the prior art, the present invention implements an electrophoresis device that may perform a process of introducing a sample into a capillary tube without immersing the capillary end into the sample storage unit for conducting electrophoresis.

Means for Solving the Problems

A capillary electrophoresis device of the present invention comprises a capillary tube, a suction pump for taking liquid, an intake tube whose end is formed vertically downward, a connection block in which there is an intake flow path that holds the end of the capillary tube and connecting the suction pump to the intake tube, a sample storage unit which contains a sample and has an upward opening into which the tip of the intake tube may be inserted, an intake tube access mechanism to insert the tip of the intake tube into the sample storage unit, and a voltage application mechanism that applies an electric potential difference across the capillary tube.

Because the configuration described above connects the suction pump and the intake tube through the intake flow path, a sample may be taken out of the tip of the intake tube. The sample storage unit has an opening on its upper part into which the tip of the intake tube may be inserted, and because there is a mechanism of accessing the intake tube that inserts the tip of the intake tube into the sample storage unit, a sample may be taken form the tip of the intake tube and placed near the end of the capillary tube.

For applying the method of immersing the injection end of a capillary tube in the sample storage unit of the prior art, it is necessary to bend the capillary tube so that the injection end points downward, and the certain capillary length is required if considering possible degradation of the resolution. This causes a problem: the longer the capillary length is, the longer the detection time. Another problem is that as the strength of electric field across the capillary tube increases for reducing the detection time, the effect of Joule heating is also intensified to broaden the sample band. Bending the capillary tube produces a region where no temperature control may be accomplished, which makes a uniform temperature distribution across the capitally tube difficult to establish. Raising the capillary temperature for reducing the migration time makes viscosity of the separation medium uneven along the length direction of the capitally tube because of existing non-controllable temperature regions including the injection end, which degrades the resolution of separation.

For the aforementioned problem, the electrophoresis device of the present invention may place a sample near the end of a capillary tube without immersing the end of the capillary tube into the sample storage unit, and therefore, a straight capillary tube may be configured horizontally. Because the capillary tube may be straight, there is no need to consider the degradation of the resolution, and the capillary length may be a minimized to reduce the separation time. By placing a straight capillary tube horizontally, it is also attainable to control the temperature uniformly.

A first preferable embodiment of the electrophoresis device of the present invention further comprises a cathode reservoir that contains a buffer solution and has an upward opening into which the tip of an intake tube may be inserted, and an anode reservoir that holds the other end of the capillary tube and forms a concavity part for containing a buffer solution and through which the capillary tube is fed, where the intake flow path is formed to transverse the end of the capillary tube, and the mechanism for accessing the intake tube may insert the intake tube into the cathode reservoir as well. The voltage application mechanism may apply the sample introduction voltage for introducing a sample into the capillary tube and the electrophoresis voltage for conducting electrophoresis.

When a separation medium is filled in the capillary tube, the configuration of the first embodiment may perform: a sample intake process where the tip of the intake tube is inserted into the sample storage unit and the suction pump takes the sample out of the sample storage unit to the intake flow path to wet the end of the capillary tube; a sample introduction process where, after the sample intake process, the tip of the intake tube is inserted into the cathode reservoir and the voltage application mechanism applies the sample introduction voltage between the cathode reservoir and the anode reservoir; a buffer solution intake process where, after the sample introduction process, the tip of the intake tube is inserted into the cathode reservoir and the suction pump takes a buffer solution from the cathode reservoir to the intake flow path to wet the end of the capillary tube; and an electrophoresis process where, after the buffer solution intake process, the electrophoresis voltage is applied between the cathode reservoir and the anode reservoir. With these processes, it is attainable to introduce a sample into a capillary tube and conduct electrophoresis analysis without immersing the end of the capillary tube and the electrodes into the sample.

The first embodiment of the present invention further comprises a control unit which controls the suction pump, the mechanism of accessing the intake tube, and the mechanism of applying voltages, where, with a separation medium filled in a capillary tube, the control unit preferably comprises a sample intake unit which carries out a sample intake process where the tip of the intake tube is inserted into the sample storage unit and the suction pump takes the sample to the intake flow path to wet one end of the capillary tube; a sample introduction unit which, after the sample intake process, the tip of the intake tube is interested into the cathode reservoir and the voltage application mechanism applies electric potential difference between the cathode reservoir and the anode reservoir; a buffer solution intake unit which, after the sample introduction process, the tip of the intake tube is inserted into the cathode reservoir and the suction pump takes a buffer solution out of the cathode reservoir to the intake flow path to wet one end of the capillary tube; and a electrophoresis unit which, after the buffer solution intake process, applies the phoresis voltage between the cathode reservoir and the anode reservoir for conducting electrophoresis. In this way, introducing a sample into the capillary tube and conducting electrophoresis may be automated.

In addition, the embodiment of the present invention further comprises a separation medium supply unit which discharges the separation medium from the tip of a nozzle, a connection port which is formed in the anode reservoir to connect the nozzle of the separation medium supply unit with the other end of the capillary tube holding fluid tight, a mechanism of driving the nozzle which connects the nozzle with the connection port or detaches the nozzle from the port, and the control unit preferably further comprises a separation medium filling unit which controls the operation of the separation medium supply unit to connects the nozzle to the connection port prior to the sample intake process for discharging the separation medium from the tip of the nozzle and filling the separation medium in the capillary tube. In this way, filling a separation medium in the capillary tube may be also automated.

Here, "fluid-tight" is a condition in which there is no leak under a certain pressure.

A second preferable embodiment of the present invention comprises a cathode reservoir which stores a buffer solution, and an anode reservoir which has a concavity for holding a buffer solution and the other end of the capillary tube is fed through the concavity, and the connection block further comprises a feed through flow path which feeds one end of the capillary tube through the cathode reservoir and at the same time intersects with the intake flow path. In this case, the voltage application mechanism applies the phoresis voltage between the cathode reservoir and the anode reservoir for moving the sample in the capillary tube.

With a separation medium filled in the capillary tube, the second embodiment of the present invention may carry out the sample intake process where the tip of the intake tube is inserted into the sample storage unit and the suction pump takes the sample and the buffer solution of the cathode reservoir simultaneously to the crossing segment of the feed through path and the intake flow path, and the electrophoresis process where, after the sample intake process, the voltage application mechanism applies the phoresis voltage between the cathode reservoir and the anode reservoir. In this way, a sample may be introduced into the capillary tube and electrophoresis may be carried out without immersing the capillary tube end and an electrode in the sample.

In the second embodiment, the cathode reservoir connects with the capillary tube through the feed through flow path, and therefore it is not required to immerse the tip of the intake tube in the cathode reservoir, and applying the phoresis voltage between the cathode reservoir and the anode reservoir may introduce the total amount of sample placed the crossing segment of the feed through path and the intake flow path into the capillary tube for performing electrophoresis.

When electrically introducing the sample in contact with the capillary tube end into the interior of the capillary tube, the amount of the sample introduced into the capillary tube is determined by the applied voltage strength and the application time. However, because each component of a sample has different electrical mobility, the amount of each component of a sample introduced in the capillary tube is different from the original composition of the sample. Thus, it is impossible to conduct a quantitative measurement for each component of a sample if such method for introducing a sample is applied. On the contrary, because the embodiment of the present invention may introduce the total amount of a sample placed in the crossing segment of the feed through path and the intake flow path for electrophoresis, it is possible to conduct a quantitative measurement of each component of the sample.

The second embodiment of the present invention further comprises a control unit which controls the suction pump, the mechanism of accessing the intake tube and the mechanism of applying voltages, and with a separation medium filled in the capillary tube, the control unit preferably has a sample intake mechanism which performs a sample intake process where the tip of the intake tube is inserted into the sample storage unit and the suction pump simultaneously takes a sample from the sample storage unit and a buffer solution from the cathode reservoir to place the sample into the crossing segment of the feed through path and the intake flow path; and, an electrophoresis unit which conducts electrophoresis where the voltage application mechanism applies the phoresis voltage between the cathode reservoir and the anode reservoir after the sample intake process. In this way, the series of processes to electrophoresis may be automated.

The second embodiment further comprises a separation medium supply unit which discharges the separation medium from the tip; a connection port, formed in the anode reservoir, connects the nozzle of the separation medium supply unit with the other end of the capillary tube maintaining fluid tight; and a mechanism of driving the nozzle which connects the nozzle with the connection port or detaches the nozzle from the port; and the control unit further has a separation medium filing unit which controls the operation of separation medium supply unit and connects the nozzle with the connection port prior to the sample intake process to discharge the separation medium from the tip of the nozzle so that the separation medium fills the capillary tube. In this way, filling a sample into the capillary tube may be automated.

A mechanism of moving the sample storage unit in the horizontal and the vertical directions configures the example of the mechanism of accessing intake tube of the electrophoresis device of the present invention.

Effect of the Invention

In the electrophoresis device of the present invention, because the suction pump and the intake tube are connected through the intake flow path, the tip of the intake tube may take a sample and place it near the end of the capillary tube. As there is a voltage application unit that applies a certain electrical potential drop across both ends of the capillary tube, the process of introducing a sample into the capillary tube and the process of electrophoresis may be carried out without immersing the capillary ends in the sample storage unit. This configuration may prevent the film coated on the capillary ends from being damaged and also eliminate a mechanism of washing the capillary ends.

DETAILED DESCRIPTION OF THE EXEMPLARY EMBODIMENTS

Figure 1:
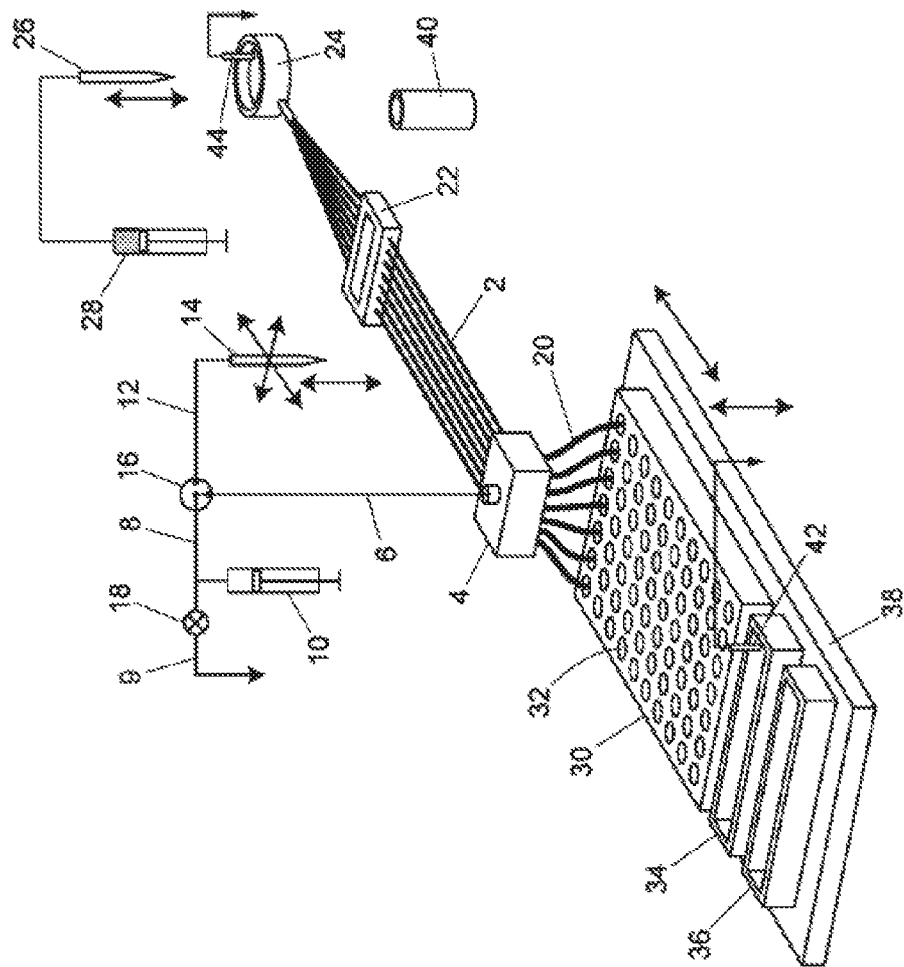
FIG. 1 A schematic diagram of an embodiment of electrophoresis device.

Referring to FIG. 1, the first embodiment of the electrophoresis device of the present invention is described hereinafter.

There are a plural number of capillary tubes 2 aligned in the horizontal direction. One ends (i.e., the intake ends) of all the capillary tubes 2 are held by a connection block 4 while they are arranged in the horizontal direction, and the other ends (i.e., the detection ends) are bundled in a single location where a common anode reservoir 24 accepts them. There is a detection unit 22 in the middle of the capillary tubes 2, and each of the capillary tubes 2 runs parallel to others from the connection block 4 to the detection unit 22 that optically detects the interiors of all capillary tubes 2.

The connection block 4 holds the same number of intake tubes 20 as the capillary tubes 2 on its lower surface of the base and one end of flow path tube 6 on its upper surface of the base. The ends of intake tubes 20 are configured to point vertically downward. Each of the intake tubes 20 is formed corresponding to each of the capillary tubes 2, and each of the capillary tubes 2 is connected to a corresponding intake tube 20 through the connection block 4. The flow path 6 feeds through all intake tubes 20 in the connection block 4.

A syringe-pump 10 attached as the intake pump takes and discharges liquid. The inlet and the outlet of the syringe pump 10 are connected with the flow path 8 that are connected to a flow path switching valve 16 and the flow path 9 connected to the drain. The flow path 8 is connected with a common port of the flow path switching valve 16. The flow path switching valve 16 has two selection ports each of which is respectively connected with a flow path 6 to the connection block 4 and with a flow path 12 to intake and discharge nozzle 14, enabling to selectively switch the flow path 8 connecting with the flow path 6, the flow path 12, or neither flow path. On the flow path 9, there is an open-close valve 18 attached to open or close the flow path.

Between the flow path switching valve 16 and the open-close valve 18, there is a syringe pump 10 attached to connect with one of the flow path 6, the flow path 9, or the flow path 12. When the syringe pump 10 connects with the flow path 6, from the syringe pump 10 to the intake tube 20 are connected through so that the syringe pump 10 may intake liquid and air from the ends of the intake tubes 20. In the description below, the flow path fed through from the syringe pump 10 to the intake tubes 20 defines an intake line.

When the syringe pump 10 connects with the flow path 12, the syringe pump 10 may take and discharge liquid from the tip of the intake-discharge nozzle 14. A driving mechanism not shown in this figure may move the intake-discharge nozzle 14 in the horizontal and the vertical directions.

When the syringe pump 10 connects with the flow path 9, the syringe pump 10 may discharge the sucked liquid to a drain. The syringe pump 10 connects with the drain as required for discharging the sucked liquid.

Figure 2:
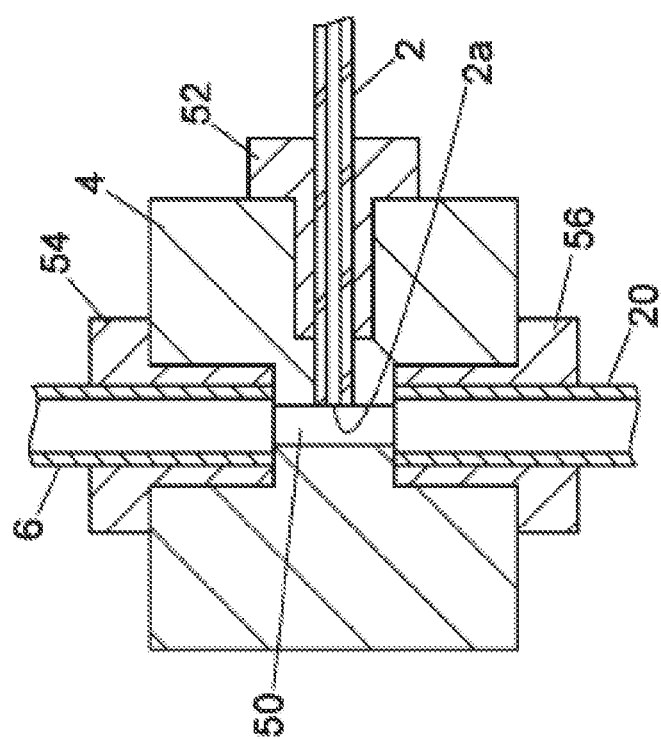
FIG. 2 A cross-sectional diagram of internal structure of connection block of the embodiment.

Referring to the schematic cross section as shown in FIG. 2, the internal structure of the connection block 4 is now described hereinafter.

The capillary tubes 2 are inserted into a side surface of the connection block 4 and fixed therein with a fixing agent 54. Tubes configuring the flow path 6 are fixed on the upper surface of the connection block with the fixing agent 52 whereas the intake tubes 20 are fixed on the lower surface of the connection block 4 with a fixing agent 56. In the connection block 4, there are a plural number of intake flow paths 50 that connect between the flow path 6 and each of intake tubes 20, crossing an end of each of the capillary tubes 2 inserted in the connection block 4.

The connection block 4 may use a three-way block which is made of polyether ether ketone (PEEK) and has a T-shaped flow path formed inside. The capillary tubes 2 are inserted into the side surface of the connection block 4 so that the capillary ends 2a reach to the crossing segment of the T-shaped flow path in the connection block 4. The tubes of the flow path 6 and the intake tubes 20 are made of, for example, polytetrafluoroethylene (PTFE).

Referring FIG. 1 again to continue describing the embodiment, an anode reservoir 24 which holds the detection ends of the capillary tubes 2 has a concavity for storing a buffer solution and connecting to the detection end of the capillary 2. Although not shown in the figure, in the connecting part between the concavity of the anode reservoir 24 and the detection end of the capillary 2, there is a connection port which fluid-tightly connects the separation medium supply nozzle 26 with the capillary 2 by inserting the tip of the nozzle 26 into the connecting part between the concavity of the anode reservoir 24 and the detection end of the capillary 2. The separation medium supply nozzle 26 connects with the separation medium injection syringe 28 so that the separation medium may be discharged from its tip. A driving mechanism not shown in the figures may move the separation medium supply nozzle 26 along the vertical direction above the anode reservoir 24.

A sample plate 30 which has a plural number of sample wells 32 (the sample storage unit), a cathode reservoir 34, and an intake line washing port 36 are configured on a moving table 38. The sample wells 32 are concavities, having upward openings, each of which stores a different sample. The sample wells 32 are configured to make a line aligned to the line of ends of intake tubes 20 so that each of the intake tubes 20 may be inserted into a separated sample well 32 simultaneously.

The cathode reservoir 34 is a container that has an upward opening for storing a buffer solution. The intake line washing port 36 also has an upward opening into which all ends of the intake tubes 20 may be inserted from the above, and stores washing water in it.

The moving table 38 moves a reaction well 32, the cathode reservoir 34 and the intake line washing port 36 in the horizontal and the vertical directions according to processes to be performed so that ends of the intake tubes 20 may be inserted.

There is also a nozzle washing port 40 formed for washing an intake-discharge nozzle 14. The nozzle washing port also stores washing water.

The anode reservoir 24 has a structure into which an anode electrode 44 may be inserted whereas the cathode reservoir 34 has a structure into which a cathode electrode 42 is inserted. The cathode electrode 42 and the anode electrode 44 form part of the voltage application mechanism for applying electric potential difference across the electrodes. The cathode electrode 42 and the anode electrode 44 may be always inserted in the anode reservoir 24 or the cathode reservoir 34, or may be inserted into the anode reservoir 24 or into the cathode reservoir 34 as required.

Figure 3:
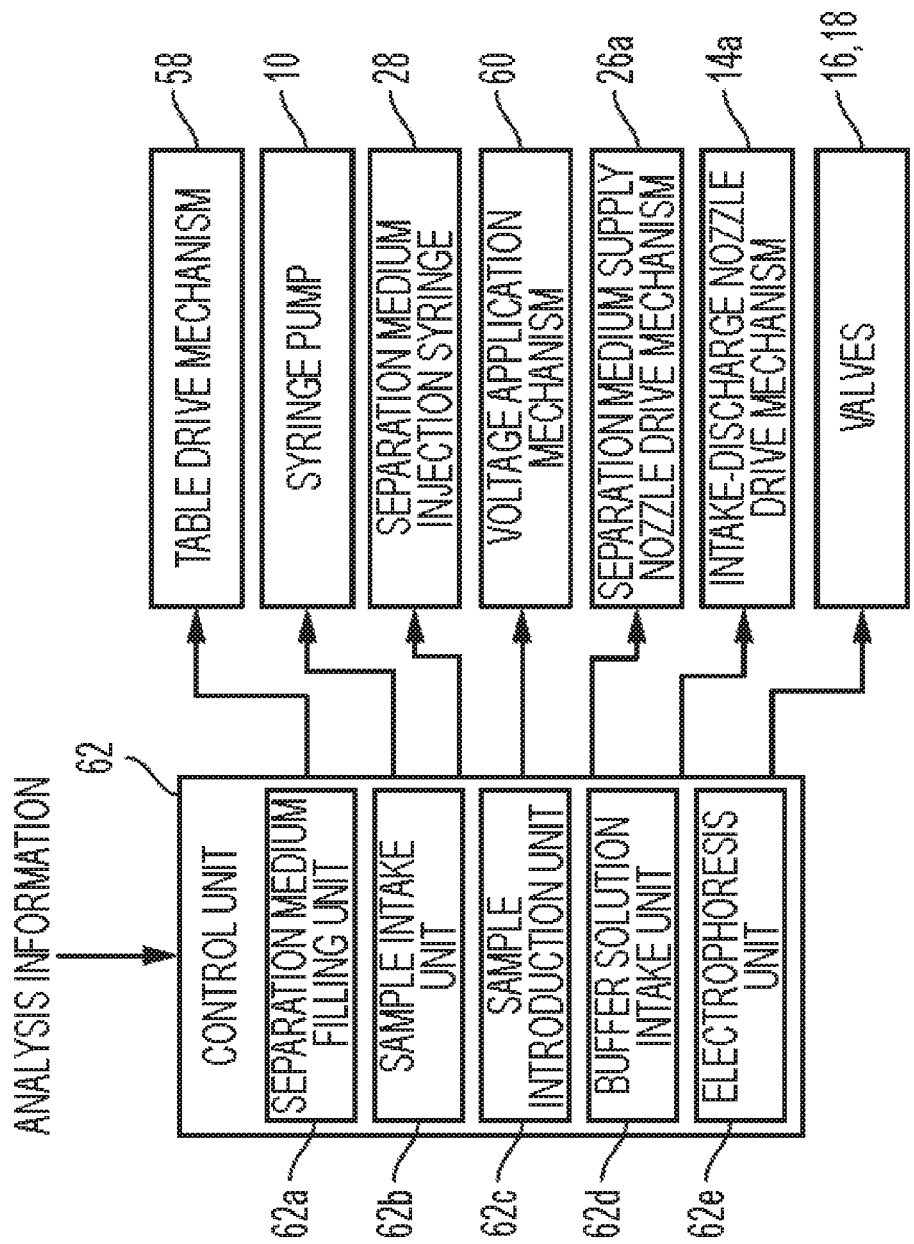
FIG. 3 A block diagram of signal system of the embodiment.

Referring to FIG. 3, the control system of the embodiment is explained hereinafter.

A control unit 62 controls operations of the syringe pump 10, the flow path switching valve 16 and the open-close valve 18 (called the valves 16 and 18, hereinafter), the separation medium injection syringe 28, the driving mechanism 14a that drives the intake-discharge nozzle 14, the driving mechanism 26a that drives the separation medium supply nozzle 26, the table driving mechanism 58 that drives the moving table 38, and the voltage application mechanism 60.

In order to perform required processes for electrophoresis analysis, the control unit 62 has a separation medium filling unit 62a, a sample intake unit 62b, a sample introduction unit 62c, a buffer solution intake unit 62d, and an electrophoresis unit 62e.

The separation medium filling unit 62a is configured to carry out a process of filling the capillary tubes 2 with a separation medium.

The sample intake unit 62b is configured to perform a process of taking a sample out of the ends of the intake tubes 20.

The sample introduction 62c is configured to carry out a process of introducing the sample taken from the ends of the intake tubes 20 into the capitally tubes 2.

The buffer solution intake unit 62d is configured to carry out a process of taking a buffer solution from the ends of the intake tubes 20.

The electrophoresis unit 62e is configured to conduct electrophoresis which migrates the sample introduced to the capillary tubes 2 in the capillary tubes.

Referring to the flowchart of FIG. 4 and FIG. 5 along with FIG. 1, the process flow of the embodiment of the electrophoresis device is explained hereinafter.

Figure 4:
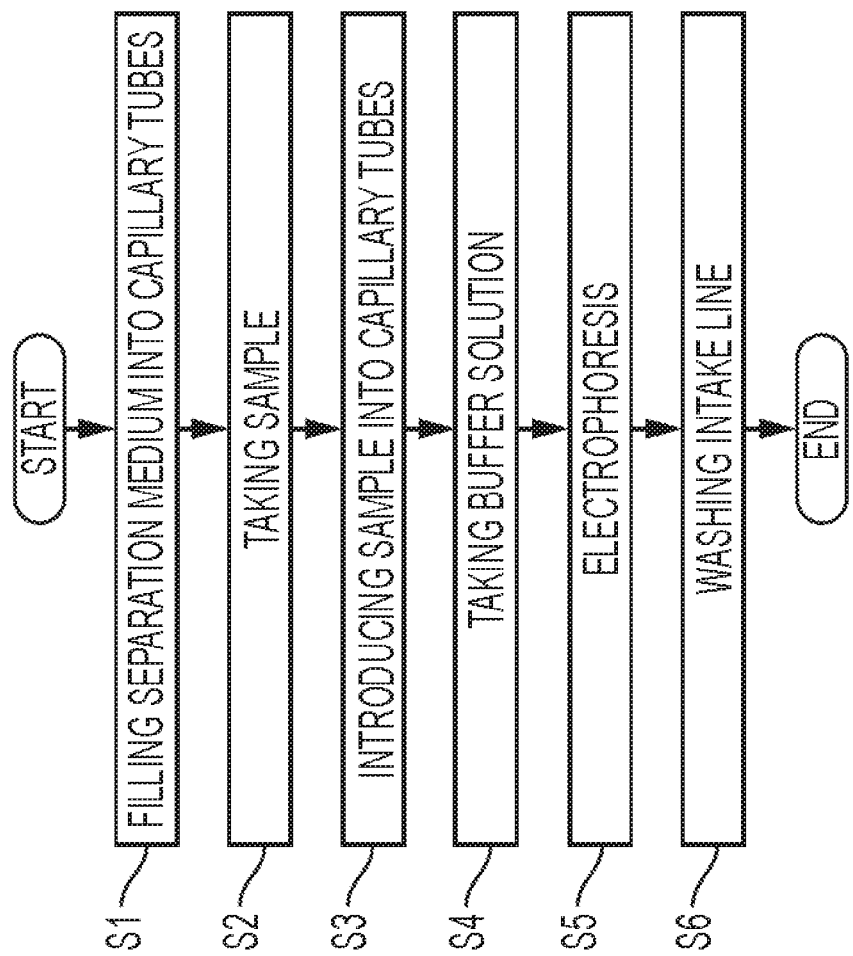
FIG. 4 A flow chart of an operational example of the embodiment.
Figure 5:
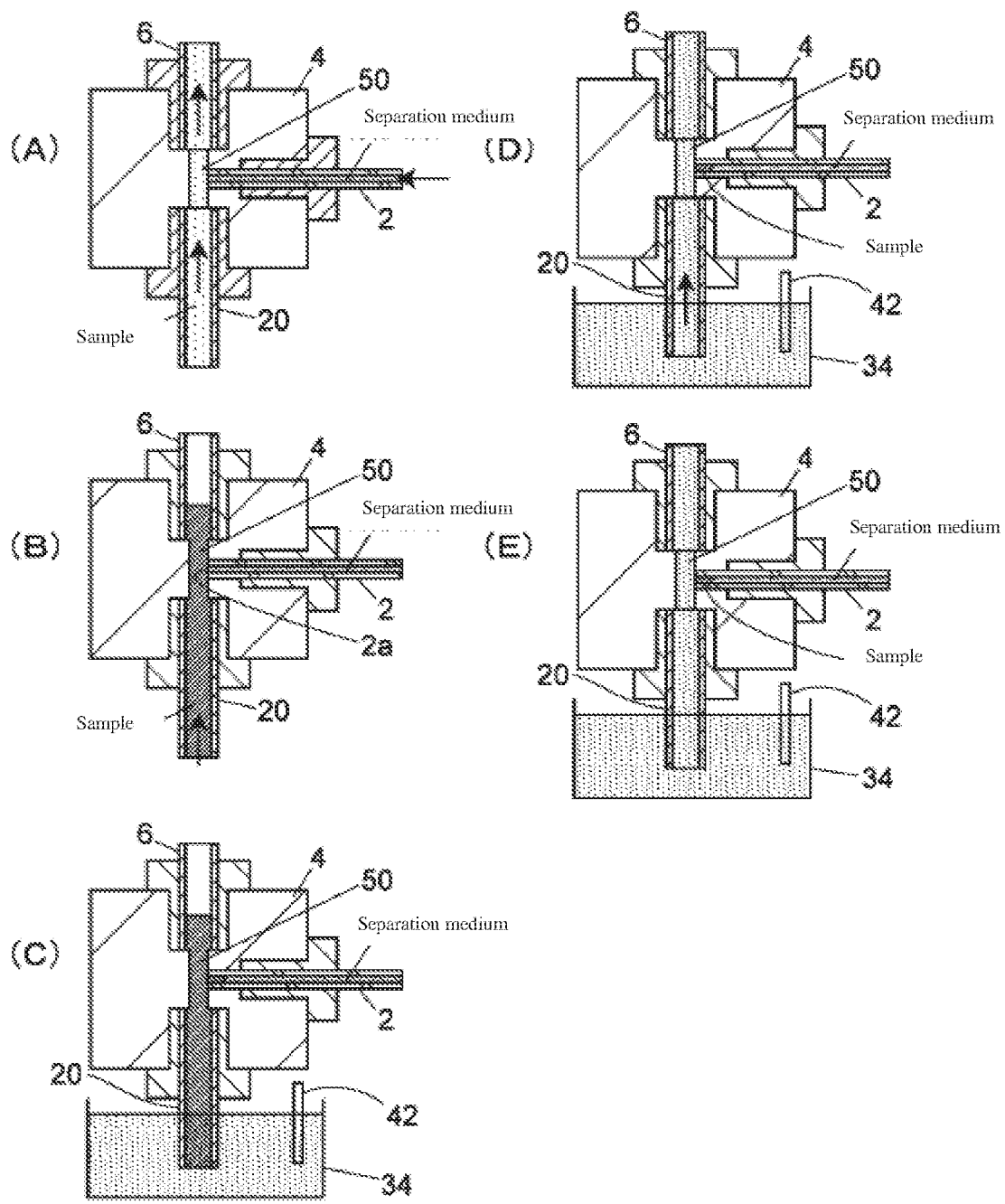
FIG. 5 A schematic diagram of condition of each process of the embodiment.

[Separation Medium Filling Process (Step S1 of FIG. 4, and FIG. 5(A))]

Prior to performing the separation medium filling process, there is no buffer solution stored in the anode reservoir 24. The step inserts the tip of the separation medium supply nozzle 26 into the anode reservoir 24 to connect the capillary tubes 2 to the separation medium injection syringe 28, and the separation medium injection syringe 28 pressure-fills a separation medium into the capillary tubes 2.

Pressure-filling a separation medium into the capillary tubes 2 is preferably carried out while immersing the ends of the intake tubes 20 in washing water of the intake line washing port 36 so that the syringe pump 10 may take washing water. With this configuration, the washing water washes out the separation medium overflown from the ends of the capillary tubes 2 in the connection block 4, and the condition of the separation medium is prepared at the ends of the capillary tubes 2.

At this moment, the syringe pump 10 connects to the intake-discharge nozzle 14 so that a buffer solution in the cathode reservoir 34 may be taken from the tip of the intake-discharge nozzle 14 and the intake buffer solution is supplied to the anode reservoir 24.

[Sample Intake Process (Step S2 of FIG. 4, and FIG. 5(B))]

This step configures the intake line, inserts the ends of the intake tubes 20 into the sample well 32, and then the syringe pump 10 takes the predetermined amount of sample so that the sample may reach to the ends 2a of the capillary tubes 2. If washing water remains in the intake line, prior to inserting the ends of the intake tubes 20 into the sample well 32, it is preferred to take air from the ends of the intake tubes 20. In this way, there is an air gap between the washing water and the residual sample in the intake line, which prevents the washing water and the sample from mixed in the intake line.

[Sample Introduction Process (Step S3 of FIG. 4, and FIG. 5(C))]

This step inserts the ends of the intake tubes 20 into a buffer solution in the cathode reservoir 34. Once the anode electrode 44 is inserted in a buffer solution of the anode reservoir and the cathode electrode 42 is inserted in a buffer solution of the cathode reservoir 34, a sample introduction voltage (e.g., 230 V/cm for 10 seconds) between the cathode electrode 42 and the anode electrode 44 so that a predetermined amount of sample may be introduced in the capillary tubes 2.

[Buffer Solution Intake Process (Step S4 of FIG. 4, and FIG. 5(D))]

While the ends of the intake tubes 20 are inserted in the cathode reservoir 34, the syringe pump 10 takes a predetermined amount of buffer solution to wet the ends of the capillary tubes 2 with the buffer solution. If the buffer solution is taken while the sample remains in the intake line, the sample may move to the ends of the capillary tubes 2 through diffusion, which would affect the outcome of electrophoresis. For this reason, prior to taking the buffer solution, it is preferred to pull the intake tubes 20 out of the cathode reservoir 34 for taking a pre-determined amount of air. In this way, there is an air gap between the buffer solution and the residual sample in the intake line, which prevents the residual sample diffuse to the end of the capillary 2.

[Electrophoresis Process (Step S5 of FIG. 4, and FIG. 5(E))]

While the ends of the intake tubes 20 are immersed in a buffer solution of the cathode reservoir 34, a phoresis voltage (e.g., 230 V/cm) is applied between the cathode electrode 42 and the anode electrode 44 for conducting electrophoresis of the sample.

[Electrophoresis Process (Step S6 of FIG. 4)]

Upon completion the electrophoresis process, the ends of the intake tubes 20 are immersed into the washing water in the intake line washing port 36, and the syringe pump 10 takes the washing water for cleaning the intake line. Liquid sucked by the syringe pump 10 is disposed to the drain.

Figure 6:
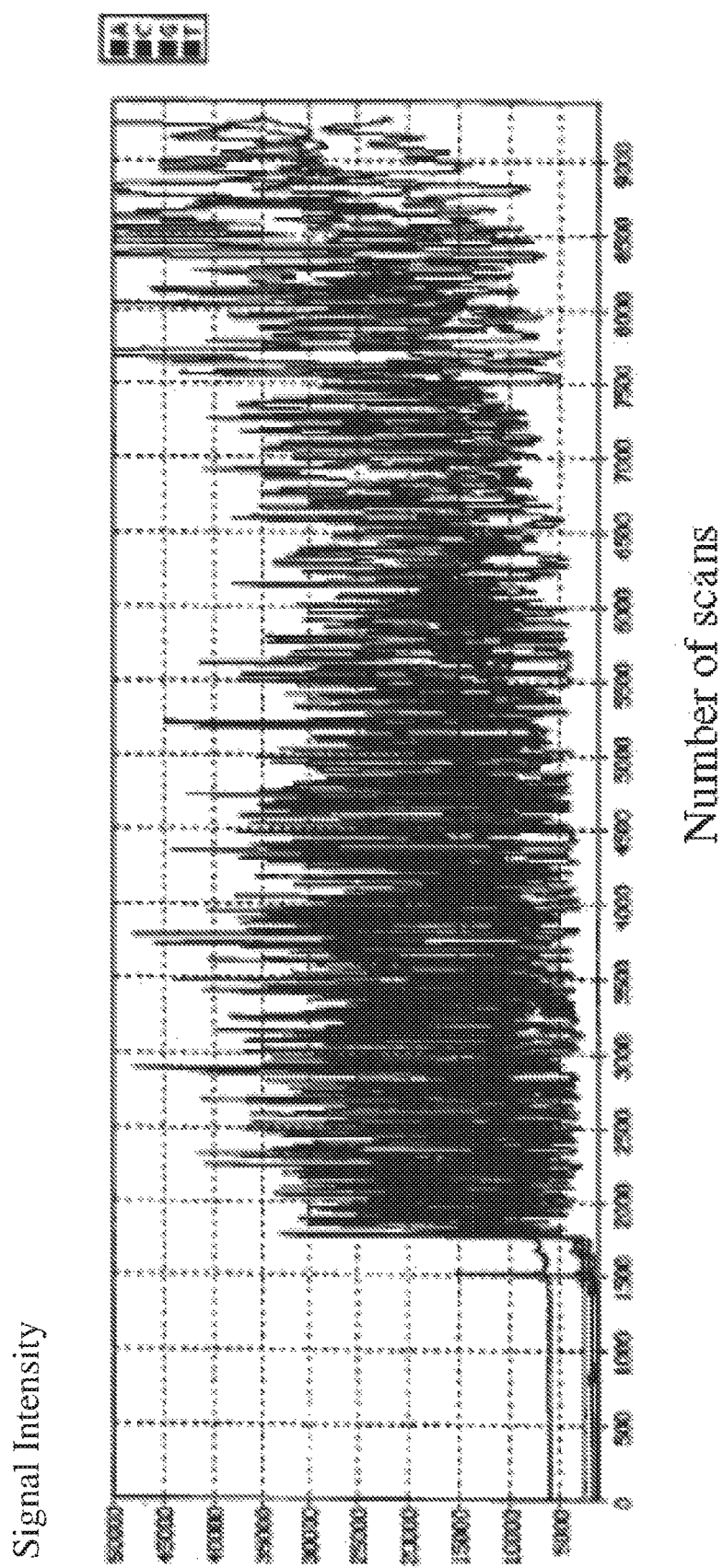
FIG. 6 An example of phoresis waveform acquired by the electrophoresis device of the embodiment.

FIG. 6 shows a phoresis waveform acquired by the electrophoresis device of the embodiment. The capillary tubes 2, each of which has the outer diameter 363 μm, the inner diameter 50 μm, the length of 170 mm (the effective length from the connection block 4 to the detection unit 22 is 85 mm), and a film coated on the inner wall for suppressing the electroosmotic flow, are used for acquiring the phoresis waveform. The separation medium is a buffer solution containing linear polyacrylamide and the buffer solution is a TTE buffer solution. The sample is mold pUC18/Primer M13-47/BigDye 3.1.

The detection unit irradiates an excitation light to the DNA sample separated by phoresis and detects the fluorescent light from the sample to obtain the phoresis waveform shown in FIG. 6. The horizontal axis represents the scanning number (the number of scanning traces) using the excitation light, and corresponds to time. The vertical axis represents the fluorescent magnitude (the signal intensity). The graph contains four major waveforms corresponding to four bases: adenine (A), guanine (G), cytosine (C), and thymine (T). From this result, the signal intensity of detected fluorescent light at each peak separated by phoresis is large, indicating that the separation is good.

Figure 7:
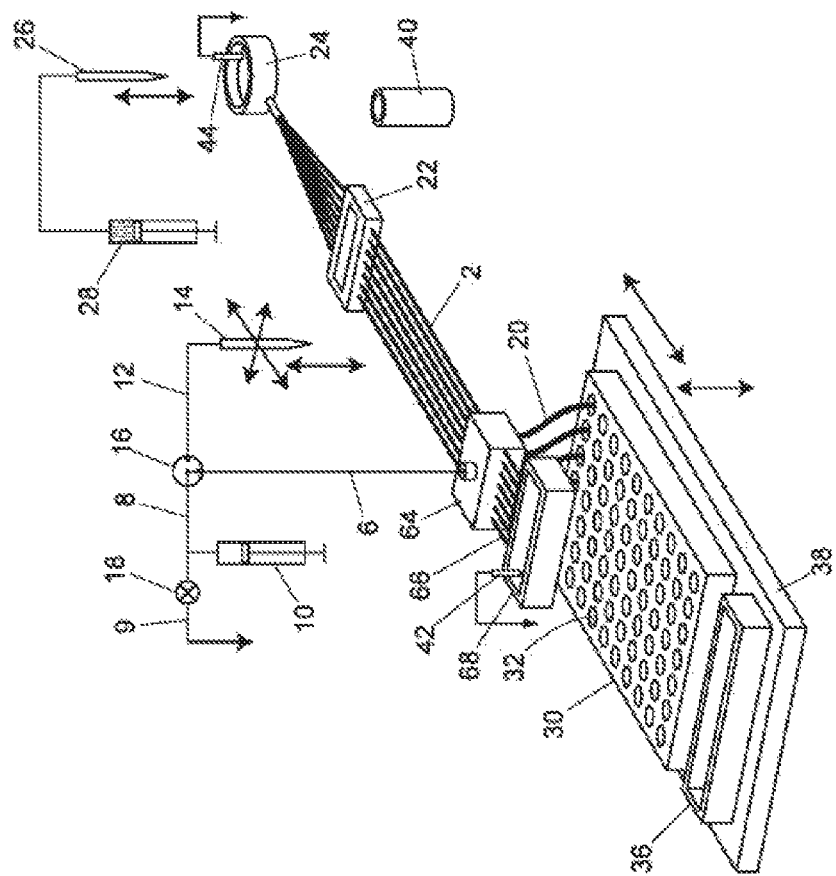
FIG. 7 A schematic diagram of another embodiment of the electrophoresis device.

Next, referring to FIG. 7, the second embodiment of the electrophoresis device is now explained hereinafter. The configured units identical to those of the first embodiment are omitted in the following description.

Instead of the connection block 4 of the first embodiment shown in FIG. 1, the second embodiment has a tube connection block 64 which has a different internal structure from the connection block 4. Similar to the connection block 4 of the first embodiment, the tube connection block 64 holds one end of the capillary 2, one end of tubes of the flow path 6, the base ends of intake tubes 20, whereas, on the other side of holding the ends of the capillary tubes 2, it holds the same number of tubes 66 as the capillary 2. One ends of the tubes 66 are attached to match with the capillary tubes 2, and the other ends are connected to the common cathode reservoir 68.

A cathode reservoir 68 replaces the cathode reservoir 34 of the first embodiment, and it stores a buffer solution into which the cathode electrode 42 is inserted. Thus, on a moving table 38, there are only a sample plate 30 and an intake line washing port 36 configured, and the cathode reservoir 68 is fixed at its position together with the connection block 64.

Figure 8:
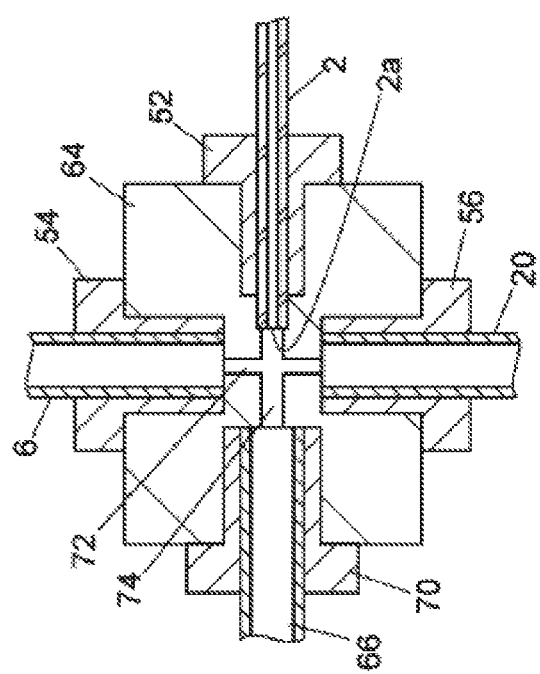
FIG. 8 A cross-sectional diagram of internal structure of connection block of the embodiment.

Referring to FIG. 8, the internal structure of the connection block 64 is explained hereinafter.

A fixing agent 52 fixes the capillary tubes 2 on one side of the connection block 64 where one ends of the capillary tubes 2 are inserted in the block. A fixing agent 54 fixes tubes of the flow path 6 on the upper surface of the connection block 64 whereas the fixing agent 56 fixes the intake tubes 20 on the lower surface of the connection block 64. A fixing agent 70 fixes tubes 66 connected to the cathode reservoir 68 on the other side surface opposite to the side surface on which the capillary tubes 2 are fixed.

In the connection block 64, there are a plural number of feed through flow paths 74 between the capillary tubes 2 inserted in the connection block 64 and corresponding tubes 66, and a plural number of intake flow paths 72 between the flow paths 6 and each of the intake tubes 20 crossing with the feed through flow paths 74. The connection block 64 may be for example a four-way arborization block made of the polyether ether ketone (PEEK) resin.

When the structure of the connection block 64 configures the intake lines from a syringe pump 10 to the intake tubes 20, the syringe pump 10 is also connected to the cathode reservoir 68. This, when the syringe pump 10 takes a sample from the ends of the intake tubes 20, a buffer solution on the cathode reservoir 68 is also taken, and at the crossing section of the intake flow path 72 and the feed through path 74 inside the connection block 64, a sample taken from the ends of the intake tubes 20 and a buffer solution taken from the cathode reservoir 68 are contacted with each other.

Figure 9:
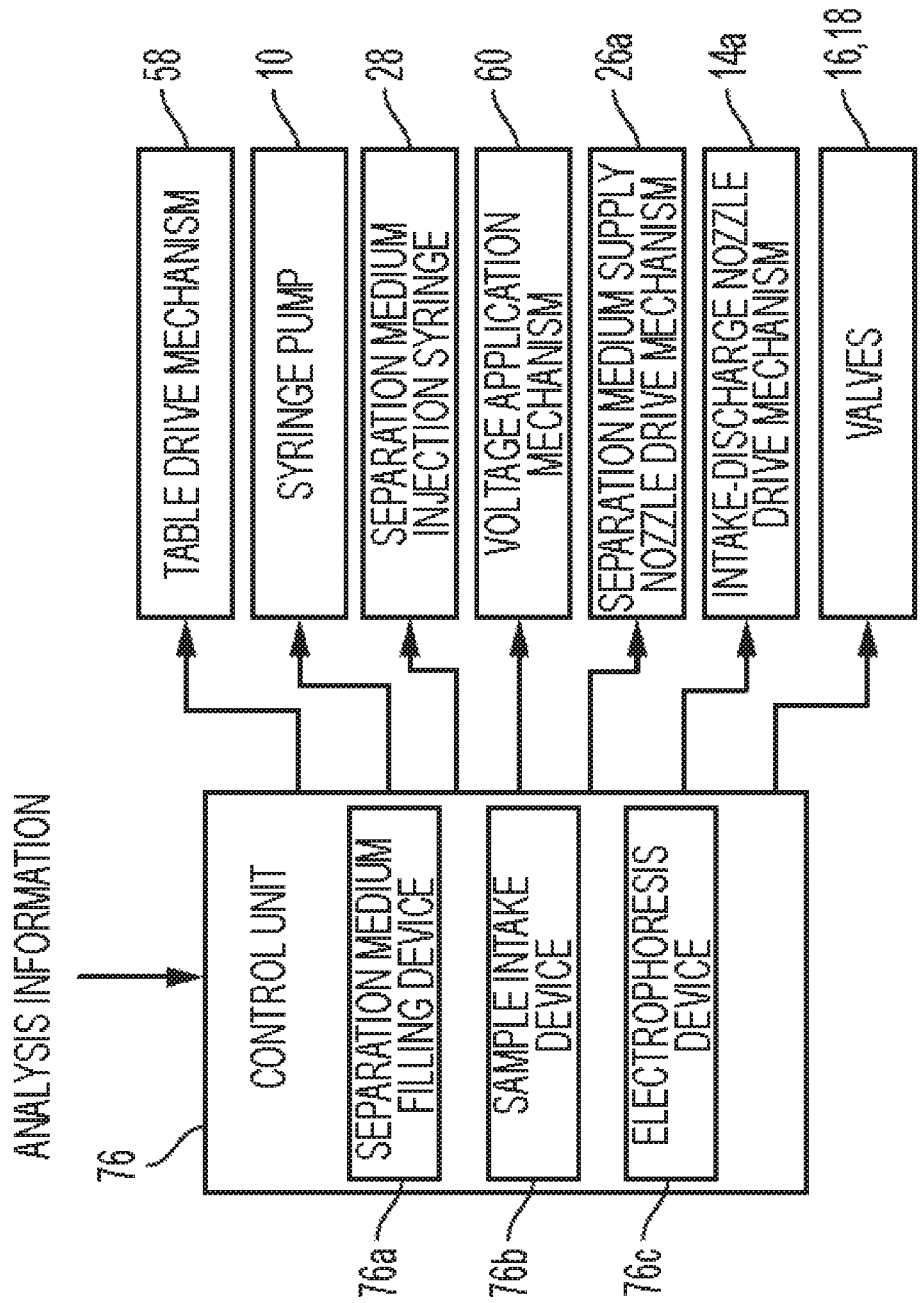
FIG. 9 A block diagram of signal system of the embodiment.

Referring to FIG. 9, a control system of this embodiment is now explained hereinafter.

A control system 76 controls the syringe pump 10, valves 16 and 18, a separation medium injection syringe 28, a mechanism of driving an intake and discharge nozzle 14a, a mechanism of driving a separation medium supply nozzle 26a, a mechanism of driving a table 58, and a mechanism of applying electric potential difference. The control unit 76 has programs for performing processes required for electrophoresis analysis: a separation medium filling device 76a, a sample intake device 76b, and an electrophoresis device 76c.

The separation medium filling device 76a is configured to carry out a process of filling a separation medium in the capillary tubes.

The sample intake device 76b is configured to carry out a process of taking a sample from a sample well.

The electrophoresis device 76c is configured to carry out an electrophoresis process.

Referring the flowchart of FIG. 10, and FIG. 11 along with FIG. 7, each process performed by the electrophoresis device of the embodiment is now described hereinafter.

Figure 10:
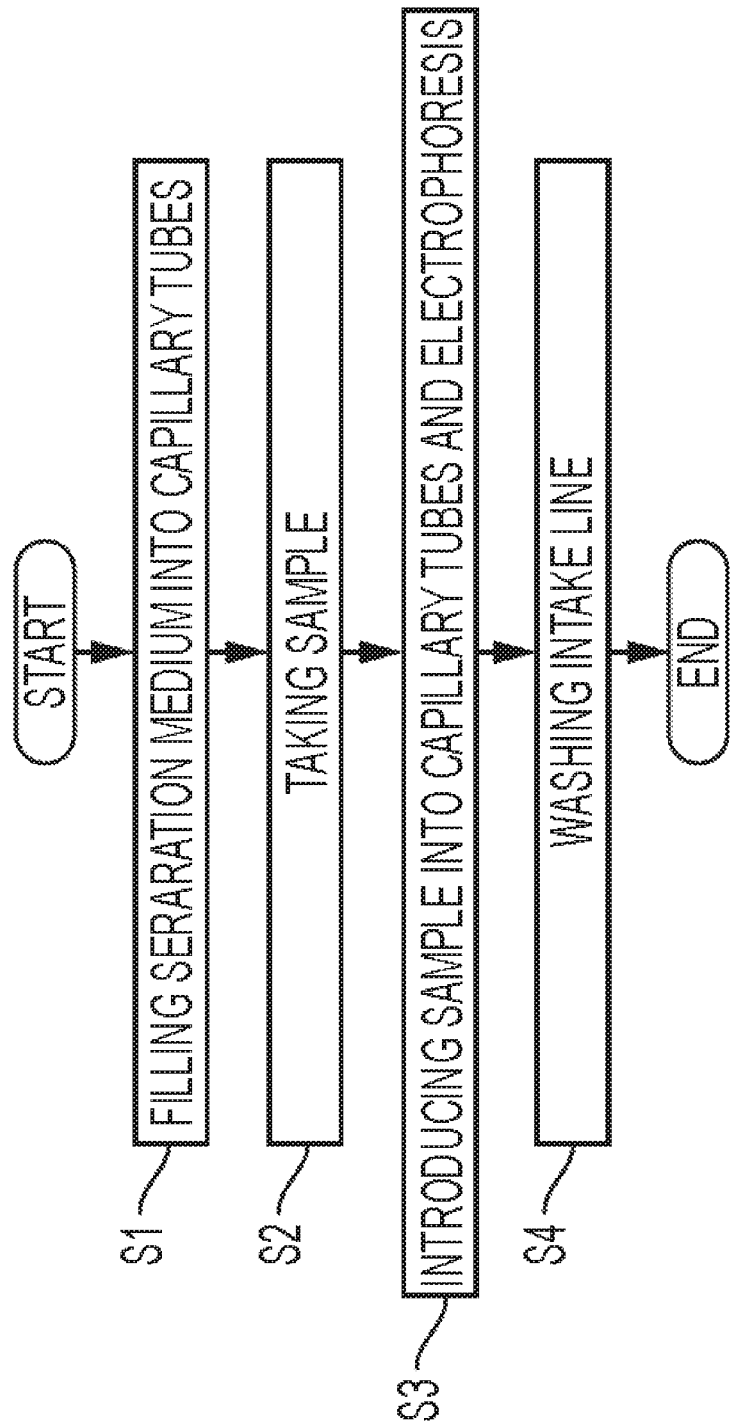
FIG. 10 A flow chart of an operational example of the embodiment.
Figure 11:
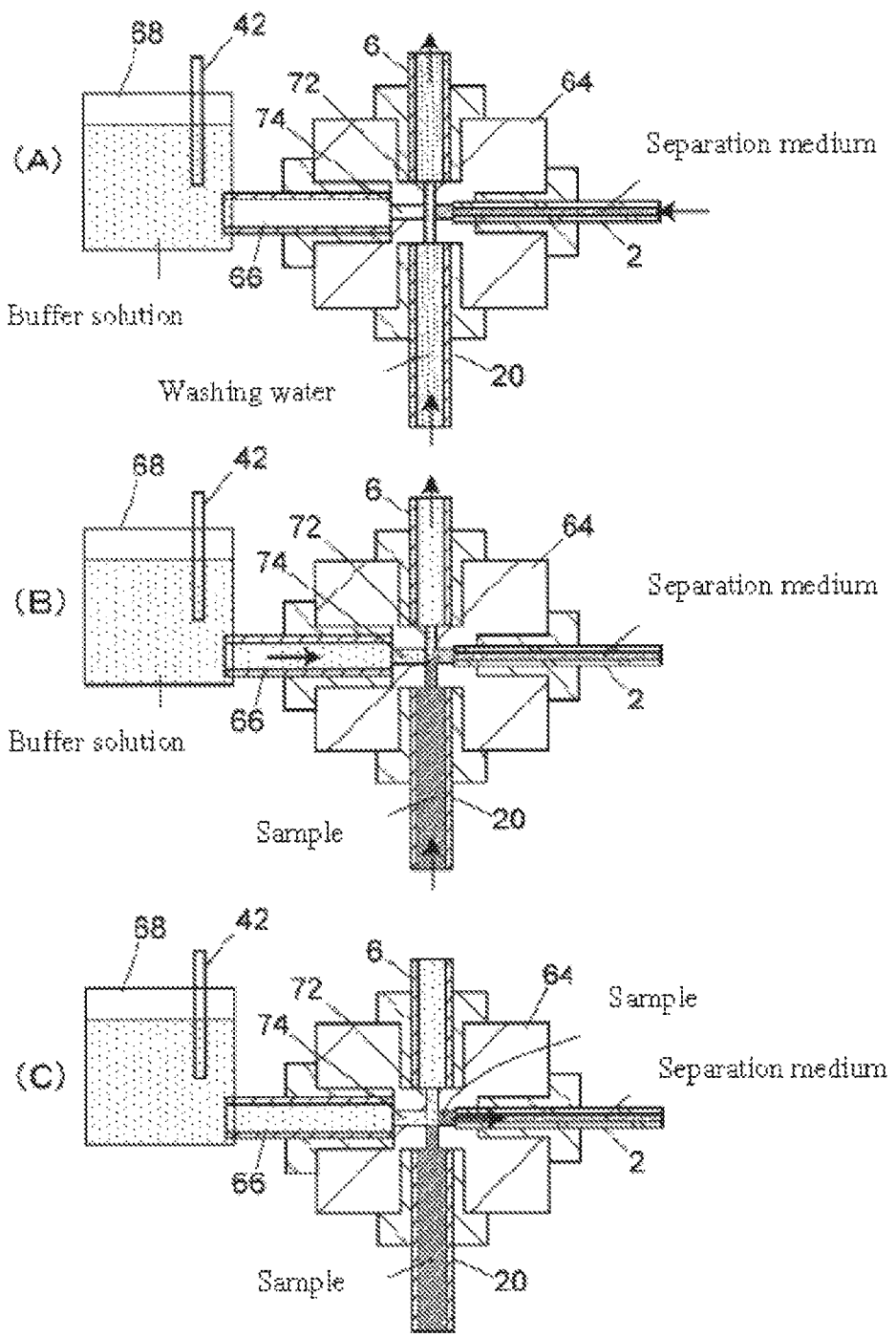
FIG. 11 A flow chart of an operational example of the embodiment.

[Separation Medium Filling Process (Step S1 of FIG. 10, and FIG. 11(A))]

Prior to performing the separation medium filling process, there is no buffer solution stored in the anode reservoir 24. Under this condition, the tip of the separation medium supply nozzle 26 is inserted into the anode reservoir 24 to connect the capillary tubes 2 to the separation medium injection syringe 28, and the separation medium injection syringe 28 pressure-fills a separation medium into the capillary tubes 2.

Pressure-filling a separation medium into the capillary tubes 2 is preferably carried out while immersing the ends of the intake tubes 20 in washing water of the intake line washing port 36 so that the syringe pump 10 may take washing water. With this configuration, the washing water washes out the separation medium overflown from the ends of the capillary tubes 2 in the connection block 4, and the condition of the separation medium is prepared at the ends of the capillary tubes 2.

At this moment, the syringe pump 10 connects to the intake-discharge nozzle 14 to take a buffer solution in the cathode reservoir 68 from the tip of the intake-discharge nozzle 14 and the intake buffer solution is supplied to the anode reservoir 24.

[Sample Intake Process (Step S2 of FIG. 10, and FIG. 11(B))]

This step configures the intake line, inserts the ends of the intake tubes 20 into the sample well 32, and the syringe pump 10 takes a sample and a buffer solution in the cathode reservoir 68 simultaneously. The amount taken by the syringe 10 corresponds to the intake the predetermined amount of the sample to be placed in the crossing segment of the intake flow path 72 and the feed through flow path 74 in the connection block 64.

[Sample Introduction Process (Step S3 of FIG. 10, and FIG. 11(C))]

This step applies a phoresis voltage (e.g., 230 V/cm) between the cathode electrode 42 immersed in the buffer solution of the cathode reservoir 68 and the anode electrode 44 immersed in the buffer solution of the anode reservoir 24. The voltage application introduces the total amount of the sample placed in the crossing segment of the intake flow path 72 and the feed through flow path 74 in the connection block 64 to the capillary tubes 2 to start conducting electrophoresis analysis.

[Buffer Solution Intake Process (Step S4 of FIG. 10)]

Upon completion the electrophoresis process, this step immerses the ends of the intake tubes 20 into the washing water in the intake line washing port 36, and the syringe pump 10 takes the washing water for cleaning the intake line. Liquid taken by the syringe pump 10 is disposed to the drain.

Figure 13:
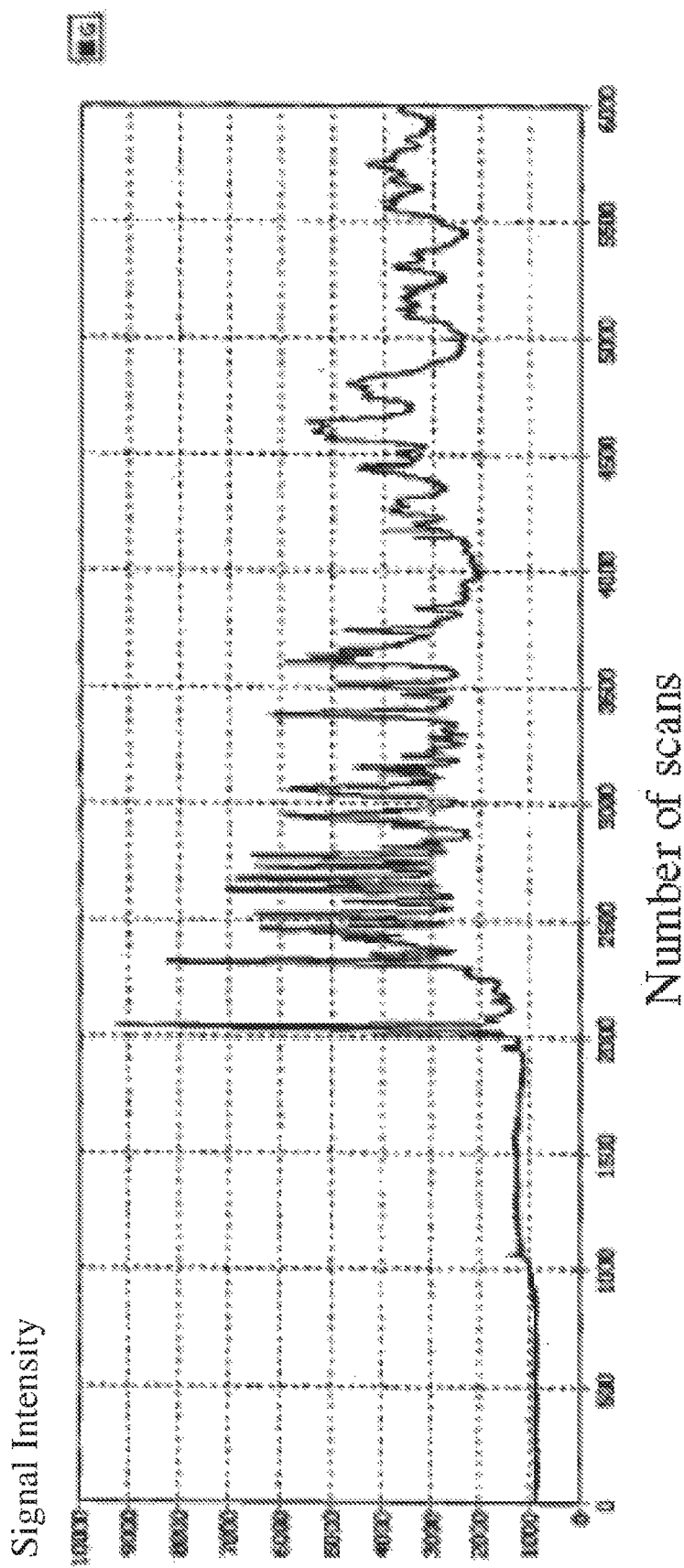
FIG. 13 An example of phoresis waveform acquired by the electrophoresis device of the embodiment.

FIG. 13 shows a phoresis waveform acquired by the electrophoresis device of the second embodiment. The capillary tubes 2, each of which has the outer diameter 363 μm, the inner diameter 50 μm, the length 170 mm (the effective length from the connection block 4 to the detection unit 22 is 85 mm), and a film coated on the inner wall for suppressing the electroosmotic flow, are used for acquiring the phoresis waveform. The separation medium is a buffer solution containing linear polyacrylamide and the buffer solution is a TTE buffer solution. The sample is mold pUC18/Primer M13-47/BigDye 3.1.

The phoresis waveform shown in FIG. 13 is obtained by the detection unit which irradiates an excitation light to the DNA sample separated by phoresis and detects the fluorescent light from a base G (guanine). The horizontal axis represents the scanning number (the number of scanning traces) using the excitation light, and corresponds to time. The vertical axis represents the fluorescent magnitude (the signal intensity). From this result, the signal intensity of detected fluorescent light at each peak separated by phoresis is large, indicating that a good separation is achieved.

Figure 12:
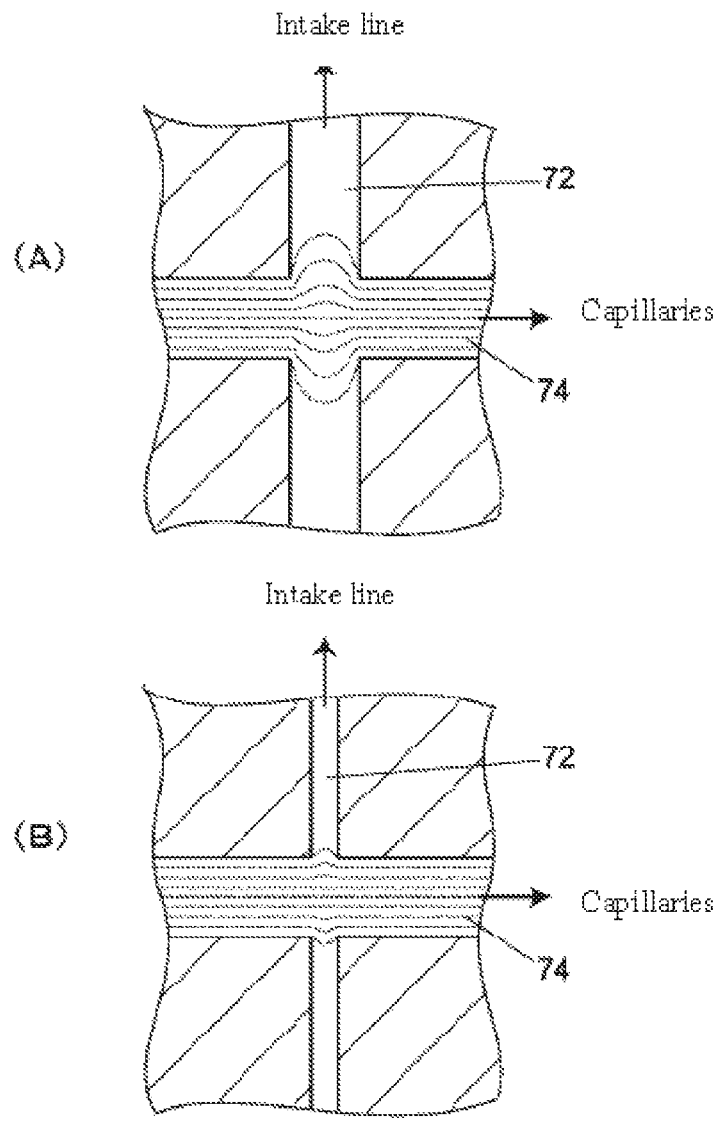
FIG. 12 A schematic diagram of condition of each process of the embodiment, where the intake flow path and the feed through path have the same cross sectional area in Figure (A), and the intake flow path has smaller cross sectional area that the feed through path in Figure (B).

In the aforementioned embodiment 2, the cross sectional area (i.e., the flow path width) of the intake flow path 72 is preferably about ⅕ to ⅓ of the cross sectional area (i.e., the flow path width) of the feed through flow path 74. FIG. 12 depicts the electric field lines of the electric field pattern formed at the time of processing electrophoresis. If the cross sectional area of the intake flow path 72 is similar to that of the feed through flow path 74, as shown in figure (A), the electric field generated in the feed through flow path 74 expands to the side of the intake flow path 72 at the crossing segment with the intake flow path 72 during the electrophoresis process, which captures samples in the upper and the lower part (the intake flow path 72) of the crossing segment and introduce them to the capillary tubes 2, causing problems such as raising the baseline of detected signals and degrading the resolution of components of slow mobility. On the other hand, as shown in figure (B), if the cross sectional area of the intake flow path 72 is about ⅕ to ⅓ of the cross sectional area of the feed through flow path 74, the electric field generated in the feed through flow path 74 is suppressed to expand to the side of the intake flow path 72, which prevents the samples in the upper and the lower part captured.

EXPLANATION OF REFERENCE NUMERALS

2 Capillary
2a Capillary end
4 and 64 Connection block
6, 8, 9, and 12 Flow path
10 Syringe pump
14 Intake-discharge nozzle
14a Mechanism of driving intake-discharge nozzle
16 Flow path switching valve
18 Open-close valve
20 Intake tube
22 Detection unit
24 Node reservoir
26 Separation medium supply nozzle
26a Mechanism of driving separation medium supply nozzle
28 Separation medium injection syringe
30 Sample plate
32 Sample well
34 Cathode reservoir
36 Intake line washing port
38 Moving table
40 Nozzle washing port
42 Cathode electrode 44 Anode electrode
50,72 Intake flow path
52, 54, 56, 70 Fixing agent
58 Mechanism of driving table
60 Mechanism of applying voltage
62, 76 Control unit
62a, 76b Separation medium filling unit
62b, 76b Sample intake unit
62c Sample introduction unit
62d Buffer solution intake unit
62e, 76c Electrophoresis unit

What is claimed:

1. A capillary electrophoresis device comprises:
a capillary tube,
a suction pump for taking liquid,
an intake tube whose end is formed vertically downward,
a connection block in which there is an intake flow path that holds the end of the capillary tube and connecting the suction pump to the intake tube,
a sample storage unit which contains a sample and has an upward opening into which a tip of the intake tube may be inserted,
an intake tube access mechanism to insert the tip of the intake tube into the sample storage unit, and
a voltage application mechanism that applies an electric potential difference across the capillary tube.

2. The capillary electrophoresis device of claim 1, wherein the capillary tube has a straight line shape and placed horizontally.

3. The capillary electrophoresis device of claim 1, further comprising:
a cathode reservoir that contains a buffer solution and has an upward opening into which the tip of an intake tube may be inserted, and
an anode reservoir that holds the other end of the capillary tube and forms a concavity part for containing a buffer solution and through which the capillary tube is fed,
where
the intake flow path is formed to transverse the end of the capillary tube, and
the mechanism for accessing the intake tube may insert the intake tube into the cathode reservoir as well, and
the voltage application mechanism may apply the sample introduction voltage for introducing a sample into the capillary tube and the electrophoresis voltage for conducting electrophoresis.

4. The capillary electrophoresis device of claim 3, further comprising a control unit which controls the suction pump, the mechanism of accessing the intake tube, and the mechanism of applying voltages, where, with a separation medium filled in the capillary tube.

5. The capillary electrophoresis device of claim 4, further comprising:
a separation medium supply unit which discharges the separation medium from a tip of a nozzle,
a connection port which is formed in the anode reservoir to connect the nozzle of the separation medium supply unit with the other end of the capillary tube holding fluid tight, and
a mechanism of driving the nozzle which connects the nozzle with the connection port or detaches the nozzle from the port.

6. The capillary electrophoresis device of claim 1, further comprising:
a cathode reservoir which stores a buffer solution, and
an anode reservoir which has a concavity for holding a buffer solution and the other end of the capillary tube is fed through the concavity,
where
the connection block further comprises a feed through flow path which feeds one end of the capillary tube through the cathode reservoir and at the same time intersects with the intake flow path, and
the voltage application mechanism applies the electrophoresis voltage between the cathode reservoir and the anode reservoir for moving the sample in the capillary tube.

7. The capillary electrophoresis device of claim 6, further comprising:
a control unit which controls the suction pump, the mechanism of accessing the intake tube and the mechanism of applying voltages, and with a separation medium filled in the capillary tube.

8. The capillary electrophoresis device of claim 7, further comprising:
a separation medium supply unit which discharges the separation medium from the tip,
a connection port, formed in the anode reservoir, connects a nozzle of the separation medium supply unit with the other end of the capillary tube maintaining fluid tight, and
a mechanism of driving the nozzle which connects the nozzle with the connection port or detaches the nozzle from the port,
where
the control unit further has a separation medium filling unit which controls the operation of separation medium supply unit and connects the nozzle with the connection port prior to the sample intake process to discharge the separation medium from the tip of the nozzle so that the separation medium fills the capillary tube.

9. The capillary electrophoresis device of claim 1, wherein the intake tube access mechanism is configured by a moving mechanism that moves the aforementioned sample storage unit in horizontal and vertical directions.

10. The capillary electrophoresis device of claim 4, wherein the control unit comprises a sample intake unit which carries out a sample intake process where the tip of the intake tube is inserted into the sample storage unit and the suction pump takes the sample to the intake flow path to wet one end of the capillary tube; a sample introduction unit which, after the sample intake process, the tip of the intake tube is interested into the cathode reservoir and the voltage application mechanism applies electric potential difference between the cathode reservoir and the anode reservoir; a buffer solution intake unit which, after the sample introduction process, the tip of the intake tube is inserted into the cathode reservoir and the suction pump takes a buffer solution out of the cathode reservoir to the intake flow path to wet one end of the capillary tube; and a electrophoresis unit which, after the buffer solution intake process, applies the electrophoresis voltage between the cathode reservoir and the anode reservoir for conducting electrophoresis.

11. The capillary electrophoresis device of claim 5, wherein the control unit further comprises a separation medium filling unit which controls the operation of the separation medium supply unit to connects the nozzle to the connection port prior to the sample intake process for discharging the separation medium from the tip of the nozzle and filling the separation medium in the capillary tube.

12. The capillary electrophoresis device of claim 7, wherein the control unit has a sample intake mechanism which performs a sample intake process where the tip of the intake tube is inserted into the sample storage unit and the suction pump simultaneously takes a sample from the sample storage unit and a buffer solution from the cathode reservoir to place the sample into the crossing segment of the feed through path and the intake flow path; and, a electrophoresis unit which conducts electrophoresis where the voltage application mechanism applies the electrophoresis voltage between the cathode reservoir and the anode reservoir after the sample intake process.

* * * * *